United States Patent [19]

Kadin

[11] 4,066,766
[45] Jan. 3, 1978

[54] 1-OXO-1H-6-SUBSTITUTED PYRIMIDO [1,2-a]QUINOLINE-2-CARBOXYLIC ACIDS AND DERIVATIVES THEREOF AND THEIR USE AS ANTIALLERGY AGENTS

[75] Inventor: Saul B. Kadin, New London, Conn.

[73] Assignee: Pfizer Inc., New York, N.Y.

[21] Appl. No.: 650,713

[22] Filed: Jan. 20, 1976

Related U.S. Application Data

[63] Continuation-in-part of Ser. No. 554,966, March 3, 1975, abandoned, and Ser. No. 547,227, Feb. 5, 1975, abandoned, and Ser. No. 456,797, April 1, 1974, abandoned.

[51] Int. Cl.² .................. A61K 31/505; C07D 471/04
[52] U.S. Cl. .............................. 424/251; 260/251 A; 260/256.4 F
[58] Field of Search .................... 260/251 A; 424/251

[56] References Cited
U.S. PATENT DOCUMENTS

| | | |
|---|---|---|
| 3,743,733 | 7/1973 | Houlihan .......................... 424/251 |
| 4,014,881 | 3/1977 | Kadin et al. .................. 260/256.4 Q |
| 4,017,625 | 4/1977 | Kadin ................................. 424/251 |

OTHER PUBLICATIONS

Gupta et al., Indian J. Chem., vol. 9, No. 3, 201-206 (1971).
Richardson et al., J. Med. Chem. 15, 1203-1206 (1972).

*Primary Examiner*—Richard J. Gallagher
*Assistant Examiner*—Diana G. Rivers
*Attorney, Agent, or Firm*—Connolly and Hutz

[57] ABSTRACT

A novel series of 1-oxo-1H-6-substituted pyrimido[1,2-a]quinoline-2-carboxylic acids of the formula

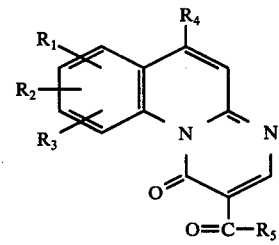

wherein each of $R_1$, $R_2$ and $R_3$ is hydrogen, alkyl having from 1 to 5 carbon atoms, alkoxy having from 1 to 5 carbon atoms, carboalkoxy having from 1 to 5 carbon atoms in the alkoxy group, fluoro, chloro, bromo, methylthio or methylsulfinyl; with the proviso that no more than two of $R_1$, $R_2$ and $R_3$ are bulky groups; i.e., branched-chain alkyl or branched-chain alkoxy, and when two of said $R_1$, $R_2$ and $R_3$ are bulky groups they are located on non-adjacent positions; $R_4$ is selected from the group consisting of chloro and bromo and $-OR_4'$ wherein $OR_4'$ is selected from the group consisting of alkoxy having from 1 to 5 carbon atoms, alkenyloxy of 3 to 4 carbon atoms and alkynyloxy of 3 to 4 carbon atoms; $R_5$ is hydroxy, alkoxy having from 1 to 5 carbon atoms and hydroxy substituted alkoxy having from 2 to 5 carbon atoms; $R_2$ and $R_3$ when taken together are 1,3-butadienyl or alkylenedioxy of one to two carbon atoms; and the pharmaceutically-acceptable cationic salts of those compounds wherein $R_5$ is hydroxy; compositions thereof; and their use as antiallergy agents.

25 Claims, No Drawings

1-OXO-6-1H-SUBSTITUTED PYRIMIDO [1,2-a]QUINOLINE-2-CARBOXYLIC ACIDS AND DERIVATIVES THEREOF AND THEIR USE AS ANTIALLERGY AGENTS

CROSS-REFERENCE TO RELATED APPLICATIONS

This application is a continuation-in-part of U.S. patent applications Ser. No. 554,966, filed Mar. 3, 1975 and now abandoned; Ser. No. 547,227, filed Feb. 5, 1975 and now abandoned; and Ser. No. 456,797, filed Apr. 1, 1974, and now abandoned.

BACKGROUND OF THE INVENTION

1. Field of the Invention

This invention relates to pyrimido[1,2-a]quinoline-2-carboxylic acids and derivatives thereof and to their use as antiallergy agents. More particularly, it relates to 1-oxo-1H-6-substituted pyrimido[1,2-a]quinoline-2-carboxylic acids wherein the substituent is chloro, bromo, alkoxy, alkenyloxy or alkynyloxy; pharmaceutically-acceptable cationic salts thereof; and derivatives thereof such as esters and amides of the 2-carboxylic acid group, and derivatives of such compounds wherein the benzenoid ring bears one or more substituents, which are useful as agents for the treatment of allergic reactions, and especially of allergic bronchial asthma.

2. Description of the Prior Art

Allergic reactions, the symptoms resulting from an antigen antibody interaction, manifest themselves in a wide variety of ways and in diffusely different organs and tissues. One of the most disabling and debilitating of the allergic reactions is asthma, a functional condition of the bronchi characterized by periodic and spasmodic attacks of breathlessness, wheezing, coughing, and expectoration of mucous.

Efforts to discover medicinal agents to alleviate the symptoms of the abnormal physiologic state have been extensive. As early as 1910, Matthews, Brit. Med. J., 1, 441 (1910) reported the bronchodilator effects of epinephrine. Since then, Chen and Schmidt, J. Pharmacol. Exper. Therap., 24, 339 (1924) reported the use of the alkaloid ephedrine as an orally efficacious bronchodilator with the same spectrum of activity as epinephrine. In 1940, Konzett, Arch. Exp. Path. Pharmak., 197, 27 (1940) outlined the effects of the potent aerossol bronchodilator isoproterenol. Cullum et al., Brit. J. Pharmacol. Exp., 35, 141 (1969) reported the pharmacology of salbutamol, a potent bronchodilator of prolonged duration, and active via both oral and aerosol administration. Many bronchodilator preparations contain theophylline. These are generally less potent than sympathomimetic amines such as isoproterenol and salbutamol, and are ineffective in aerosol administration.

Recently, Cox and co-workers, Adv. In Drug Res., 5, 115 (19870) described the pharmacology of disodium cromoglycate [1,3-bis(2-carboxychromon-6-yloxy)-2-hydroxypropane, Intal], an agent useful in the treatment of bronchial asthma. It is not a bronchodilator but mediates its therapeutic effects by a unique mechanism of action. It suffers from the lack of oral efficacy and, for optimum results, is administered by inhalation as a solid inhalant.

Although the aforementioned agents represent outstanding contributions toward the treatment of asthma, many of them exert the undesired side effect of cardiac stimulation.

The synthesis of a 1H-pyrimido[1,2-a]quinoline appears to have first been reported by Antaki et al., J. Chem. Soc., pp. 551-555 (1951) who condensed 2-chloroquinoline with ethyl β-amino crotonate in the presence of anhydrous potassium carbonate and a trace of copper bronze to produce 1-oxo-1H-3-methyl-pyrimido[1,2-a]quinoline. No utility for the compound was reported.

Antaki, J. Am. Chem. Soc., 80, 3066-9 (1958), reports the condensation of 2-aminoquinoline and ethylethoxymethylenecyanoacetate to give ethyl 2-quinolyaminomethylenecyanoacetate which when distilled under reduced pressure afforded 1-oxo-1H-pyrimido[1,2-a]quinoline-2-carbonitrile. The compound demonstrated antischistosomal action.

The synthesis of a series of 1-oxo-1H-pyrimido[1,2-a]benzimidazole-2-carboxylic acids and esters is reported by Dunwell et al., J. Chem. Soc. (Perkin I), No. 15, 1588-1590 (1973), and by Chow et al., J. Hetero. Chem., 10, 71-75 (1973). No reference to the utility of the compounds is presented.

A representative compound of the above series of compounds; namely, ethyl 1-oxo-1H-pyrimido[1,2-a]benzimidazole-2-carboxylate, when tested for antiallergy activity by the passive cutaneous anaphylaxis (PCA) test (Ovary, J. Immun., 81, 355, 1958) described below, was found to be inactive.

Richardson et al., J. Med. Chem., 15, 1203-6 (1972) describe ethyl 1-oxo-1H-pyrimido[1,2-a]quinoline-2-carboxylate and report it to be inactive as an antimicrobial agent. When tested for antiallergy activity by the PCA test it was found to exhibit 100% inhibition at 3 mg./kg. by the intravenous (I.V.) route of administration but is without activity at 1 mg./kg. I.V. Approximately 90% inhibition is demonstrated at 30 mg./kg. by the oral route of administration, but oral activity is absent at a dosage level of 10 mg./kg. via the oral route.

Gupta et al., Indian J. Chem., 9, 201-206 (1971) report the preparation of a compound identified as ethyl 1-oxo-1H-6-hydroxypyrimido[1,2-a]quinoline-2-carboxylate and its investigation as a hypoglycemic agent. The corresponding acid, 1-oxo-1H-6-hydroxpyrimido[1,2-a]quinoline-2-carboxylic acid, when tested for antiallergy activity by the PCA test, exhibited 83% inhibition at 30 mg./kg. I.V. and 8% exhibition at 3 mg./kg. I.V. No activity was exhibited by the oral route of administration at 3 mg./kg.

The 6-chloro analog, ethyl 1-oxo-1H-6-chloropyrimido[1,2-a]quinoline-2-carboxylate, when tested by the PCA test, was found to exhibit 82% and 19% inhibition at 3 mg./kg. and 1 mg./kg., respectively, via the I.V. route of administration. No practical oral activity was exhibited at 30 mg./kg.

SUMMARY OF THE INVENTION

It has now been found that compounds of formula I

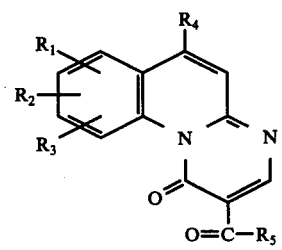

are effective antiallergy agents. In formula I, each of the benzenoid substutients $R_1$, $R_2$ and $R_3$ is selected from the group consisting of hydrogen, alkyl having from 1 to 5 carbon atoms, alkoxy having from 1 to 5 carbon atoms, carboalkoxy having from 1 to 5 carbon atoms in the alkoxy group, fluoro, chloro, bromo, methylthio and methylsulfinyl; with the proviso that no more than two of $R_1$, $R_2$ and $R_3$ are bulky groups; i.e., branched chain alkyl or branched chain alkoxy, and when two of said $R_1$, $R_2$ and $R_3$ are bulky groups they are located on non-adjacent positions;

$R_2$ and $R_3$ when taken together are selected from the group consisting of 1,3-butadienyl and alkylenedioxy of 1 to 2 carbon atoms;

$R_4$ is selected from the group consisting of chloro, bromo and $-OR_4'$ wherein $OR_4'$ is selected from the group consisting of alkoxy having from 1 to 5 carbon atoms, alkenyloxy of 3 to 4 carbon atoms or alkynyloxy of 3 to 4 carbon atoms;

$R_5$ is selected from the group consisting of hydroxy, alkoxy having from 1 to 5 carbon atoms and hydroxy substituted alkoxy having from 2 to 5 carbon atoms;

and the pharmaceutically-acceptable cationic salts of those compounds wherein $R_5$ is hydroxy.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as triethylamine, tri-n-butylamine, piperidine, triethanolamine, diethylaminoethylamine, N,N'-dibenzylethylenediamine and pyrrolidine.

The favored compounds of formula I are those wherein not more than two bulky, i.e., branched-chain alkyl or branched-chain alkoxy, groups are present in the benzenoid ring. Compounds of particular interest are those wherein up to two substituents are present in the benzenoid ring.

Compounds of formula I of special interest to this invention are those wherein the benzenoid variables ($R_1$–$R_3$) are hydrogen and those wherein at least one and not more than two of the benzenoid substituents $R_1$, $R_2$ or $R_3$ is lower alkoxy, or fluoro, the remaining benzenoid substituents being hydrogen.

| $R_1$ | $R_2$ | $R_3$ | $R_5$ | $R_4$ |
|---|---|---|---|---|
| H | H | H | alkoxy, OH | $OCH_3$, $OC_2H_5$ |
| H | $CH_3$ | H | alkoxy, OH | $OCH_3$ |
| H | $OCH_3$ | H | alkoxy, OH | $OCH_3$ |
| H | $OC_2H_5$ | H | alkoxy, OH | $OCH_3$ |
| H | F | H | alkoxy, OH | $OCH_3$ |

The antiallergy property of the compounds of this invention is evaluated by the passive cutaneous anaphylaxis (PCA) test (Ovary, *J. Immun.*, 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

DETAILED DESCRIPTION OF THE INVENTION

The compounds of this invention are readily prepared by condensation of the appropriate 2-amino-4-($R_4$-substituted)quinoline with the appropriate dialkyl ethoxymethylenemalonate to produce the corresponding intermediate dialkyl 4-($R_4$-substituted)-2-quinolylaminomethylenemalonate which is then cyclized to the desired alkyl 1-oxo-1H-6-($R_4$-substituted)-pyrimido[1,2-a]quinoline-2-carboxylate of formula I.

The condensation is carried out by heating a stoichiometric mixture of the 2-aminoquinoline reactant and the dialkyl ethoxymethylenemalonate at a temperature of from about 80° C. to about 125° C. Lower temperatures are not desirable because the reaction proceeds at too slow a rate. Higher temperatures can be used but appear to offer no advantages. The reaction is thus conveniently carried out as a melt. It can, of course, be conducted in a solvent or mixture of solvents; for example, ethanol, N,N-dimethylformamide, acetonitrile. However, from a practical standpoint, a solvent appears unnecessary.

The condensation, when conducted under the above conditions, produces the intermediate dialkyl 4-($R_4$-substituted)-2-quinolylaminomethylenemalonate. This intermediate is then cyclized, preferably thermally, to the corresponding alkyl 1-oxo-1H-6-alkoxypyrimido[1,2-a]quinoline-2-carboxylate. The cyclization is accomplished by heating the intermediate dialkyl 4-($R_4$-substituted)-2-quinolylaminomethylenemalonate to a temperature of from about 175° C. to about 250° C. until cyclization is essentially complte, usually in about one to two hours. The cyclization is advantageously achieved by heating the intermediate in a suitable reaction-inert diluent; that is, in a compound which permits control of the reaction temperature, is stable to the relatively high temperatures employed and which does not react with the starting material or the products of cyclization. Representative of such diluents are high boiling hydrocarbons such as perhydronaphthalene, mineral oil, diethylbenzene, acetic anhydride containing sulfuric acid, diphenyl ether and diphenyl, especially that which contains 26.5% diphenyl and 73.5% diphenyl ether and is sold under the trademark Dowtherm A.

It is evident that the condensation and cyclization steps can be conducted in a single operation without the need for separating the intermediate dialkyl 4-($R_4$-substituted)-2-quinolylaminomethylenemalonate simply by employing a sufficiently high reaction temperature. The overall reaction is advantageously carried out in a suitable diluent to permit close control of the reaction temperature.

The favored procedure comprises the two steps of condensation and cyclization described above. Isolation of the intermediate compound and subsequent purification thereof before cyclization generally afford a better quality cyclized product. The esters, intermediates for corresponding acids, are prepared by choice of the appropriate dialkyl ethoxymethylenemalonate according to the preferred method of preparation described above. Alternatively, the esters are prepared by a base-catalyzed transesterification process. This method is favored when the ester moiety $R_5$ is hydroxy substituted alkoxy since the necessary di(hydroxy substituted alkoxy)ethoxymethylenemalonate reactants are not readily available. The process comprises treating an alkyl ester (a compound wherein $R_5$ is alkoxy) with an alkylene glycol, preferably in the presence of a catalytic amount of a base (i.e., from about 5% to about 20% by weight based upon the alkylene glycol used) such as triethylamine or calcium hydroxide, in air at a temperature of from about 20° C. to about 50° C. Higher temperatures can be used but appear to offer no advantage.

Compounds wherein any of $R_1$, $R_2$ or $R_3$ is methylsulfinyl are readily prepared from the corresponding thioether compounds by oxidation with an appropriate oxidizing agent such as hydrogen peroxide or a peracid such as m-chloroperbenzoic acid according to methods known to those skilled in the art. Combinations of methylsulfinyl with methylthio in the same compound are achieved by reacting, for example, a compound of formula I or the appropriate aniline (Preparation A) wherein at least two of $R_1$, $R_2$ or $R_3$ are chloro with sufficient sodium methyl mercaptide to replace only one chloro substituent. A mixture of isomers is, of course, normally formed. The monomethyl derivative is then oxidized to the sulfinyl derivative and the remaining chloro substituent or substutients replaced with methylthio in the manner described.

Compounds of formula I wherein $R_4$ is chloro or bromo serve as intermediates for compounds wherein $R_4$ is an ether group ($OR_4'$) as defined above. Replacement of the chloro or bromo substituent is readily achieved by treatment with the appropriate alcohol ($R_4'OH$) in the presence of p-toluenesulfonic acid monohydrate at about 50° C.–100° C.

Compounds of this invention wherein $R_5$ is hydroxy are conveniently prepared by hydrolysis, preferably acid hydrolysis, of the corresponding esters. The usual conditions comprise heating an aqueous mixture of the appropriate ester ($R_5$ of formula is alkoxy) and a mineral acid such as hydrochloric, sulfuric, phosphoric or nitric acids, from about 50° C. to about 100° C. for periods of up to four hours or until hydrolysis is essentially complete. The favored mineral acid is hydrochloric acid of from 3N to 12N concentration. The less soluble the compound of formula I in water, the more concentrated the acid used for hydrolysis. The free acids generally crystallize from the hydrolysis reaction mixture upon cooling and are recovered by filtration. When crystallization does not occur the acids are recovered by evaporation of the reaction mixture. The acids are purified by recrystallization from suitable solvents, such as N,N-dimethylformamide.

The acids in turn serve as intermediates for the pharmaceutically-acceptable cationic salts of this invention. Salt formation is accomplished by reacting the appropriate acid with the appropriate metal salt, such as a carbonate, bicarbonate, acetate, hexanoate, hydroxide, in suitable medium such as water, methanol or ethanol according to well-known procedures. The salts are recovered by standard methods such as by filtration if they are insoluble in the medium, by evaporation of the solvent if they are soluble in the medium, or by precipitation by addition of a non-solvent for the salt.

The 2-amino-4-ether substituted quinoline reactants are readily prepared by reaction of the corresponding 2-amino-4-hydroxyquinoline with the appropriate alkyl, or alkenyl ester of an arylsulfonic acid, such as an alkyl-p-toluenesulfonate or an alkyl ester of sulfuric acid. Alternatively, they are prepared by reaction of a metal salt—usually the sodium salt—of the sppropriate 2-amino-4-hydroxyquinoline with the appropriate alkyl, alkenyl or alkynyl halide. The amino group is protected by acetylation, if necessary, to avoid alkylation.

Many of the requisite 2-amino-4-hyroxyquinolines are described in the literature. Those that are not described in the art are easily prepared by known procedures such as by reaction of the appropriate anilinium p-toluenesulfonate or benzenesulfonate with ethyl cyanoacetate as described by Hardman et al., *J. Chem. Soc.*, 3878–3884 (1954).

Compounds of this invention wherein any of $R_1$, $R_2$ or $R_3$ is methylsulfinyl are readily prepared from the corresponding methylthio compounds by oxidation with an appropriate oxidizing agent such as hydrogen peroxide or a peracid such as m-chloroperbenzoic acid according to methods known to those skilled in the art. The methylthio compounds are, in turn, readily prepared by the reaction of the corresponding chloro compounds with sodium methyl mercaptide. Modifications of this method are obvious to those skilled in the art. For example, the methylthio ether can be made by in situ formation of the methyl mercaptide salt.

The products of this invention and the pharmaceutically-acceptable cationic salts thereof, are useful for the control of allergic symptoms and reactions in mammals, including man, and can be administered either as individual therapeutic agents or as mixtures of therapeutic agents, for example, with theophylline or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, compounds of this invention which are active can be administered orally in tablet form in admixture with excipients such as lactose, sodium citrate, calcium carbonate and dicalcium phosphate. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine, and chloroform and their combinations can be employed as well as other materials.

For the purpose of parenteral administration and inhalation, solutions or suspensions of these compounds in sesame or peanut oil or in aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds can be administered to asthmatic subjects suffering from bronchoconstriction by means of inhalators or other devices which permit the active compounds to come into direct contact with the constricted areas of the tissues of the subject.

When administered by inhalation, the compositions can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for adminstration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent of from about 1:0.5 to about 1:1.5.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The PCA reaction test procedure employed to evaluate the compounds of the present invention demonstrates an excellent correlation between activity for compounds in this test and their utility in the control of allergic asthma. The ability of agents to interfere with PCA reactions is measured in male Charles River Wistar rats, 170–210 g. Reaginic antisera is prepared according to Mota, *Immunology*, 7,681 (1964) using hen egg albumin and B. pertussis. Hyperimmune antisera to hen egg albumin is prepared according to Organe, et al., *J. Exptl. Med.*, 127, 767 (1968). Forty-eight hours prior to antigen challenge the reaginic antisera is injected intradermally (i.d.) into the shaved skin of a normal rat's back; five hours before challenge the hyperimmune antisera is similarly injected; five hours later, at a third site. 60 mcg. histamine dihydrochloride is injected i.d. as a check for antihistaminic and unspecific types of blockage, the compounds of the instant invention or saline are then administered i.v. and immediately followed by 2.5 mg. Evan's Blue dye and 5 mg. egg albumin in saline. In the case of oral administration, Evan's Blue dye and egg albumin are given five minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of 8 animals and compared to the saline treated controls. The difference is expressed as percent blockade due to the compound employed.

Compounds representative of those in the present invention are tested by the aforementioned procedure, and the resulting activities are reported as the degree (%) of protection. Disodium cromoglycate, a commercial antiallergy agent, is included for comparison.

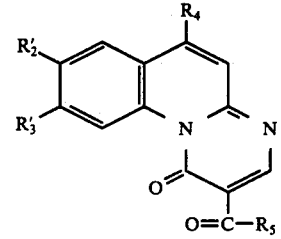

| $R_4$ | $R_2'$ | $R_3'$ | $R_5$ | I.V. mg/kg | % | Oral mg/kg | % |
|---|---|---|---|---|---|---|---|
| $OCH_3$ | H | H | $OC_2H_5$ | 3 | 92 | 3 | 100 |
|  |  |  |  | 0.3 | 72 | 1 | 86 |
|  |  |  |  | 0.03 | 28 | 0.3 | 25 |
| $OCH_3$ | H | H | OH | 3 | 100 | 3 | 98 |
|  |  |  |  | 0.3 | 72 | 1 | 78 |
|  |  |  |  | 0.03 | 31 | 0.3 | 50 |
|  |  |  |  |  |  | 0.1 | 0 |
| $OCH_3$ | $OCH_3$ | H | $OC_2H_5$ | 3 | 81 | 3 | 10 |
| $OCH_3$ | $CH_3$ | H | $OC_2H_5$ | 3 | 58 | 3 | 0 |
| $OCH_3$ | $CH_3$ | H | OH | 3 | 90 | 3 | 21 |
|  |  |  |  | 0.3 | 65 |  |  |
| $OCH_3$ | H | $OCH_3$ | $OC_2H_5$ | 3 | 13 |  |  |
| $OCH_3$ | H | $OCH_3$ | OH | 30 | 92 |  |  |
|  |  |  |  | 3 | 61 |  |  |
| $OCH_3$ | H | Cl | $OC_2H_5$ | 3 | 30 |  |  |
| $OCH_3$ | H | Cl | OH | 3 | 17 |  |  |
| $OCH_3$ | $OCH_3$ | $OCH_3$ | $OC_2H_5$ | 30 | 87 |  |  |
|  |  |  |  | 3 | 0 |  |  |
| $OCH_3$ | $OCH_3$ | $OCH_3$ | OH | 3 | 11 |  |  |
| $OCH_3$ | $OCH_3$ | H | OH | 3 | 94 |  |  |
|  |  |  |  | 0.3 | 52 |  |  |
| $OCH_3$ | $OC_2H_5$ | H | $OC_2H_5$ | 3 | 73 |  |  |
| $OCH_3$ | Cl | H | $OC_2H_5$ | 3 | 0 |  |  |
| $OCH_3$ | Cl | H | OH | 3 | 93 |  |  |
|  |  |  |  | 0.3 | 24 |  |  |
| $OC_2H_5$ | H | H | OH | 0.3 | 82 | 10 | 76 |
|  |  |  |  |  |  | 3 | 56 |
|  |  |  |  |  |  | 1 | 29 |
| $OCH_3$ | H | F | OH | 0.3 | 48 | 10 | 84 |
|  |  |  |  |  |  | 3 | 46 |
|  |  |  |  |  |  | 1 | 47 |
| $OCH_3$ | F | H | OH | 0.3 | 54 | 10 | 98 |
|  |  |  |  |  |  | 3 | 60 |
|  |  |  |  |  |  | 1 | 61 |
| Cl | H | H | $OC_2H_5$ | 3 | 82 | 30 | 29 |
|  |  |  |  | 1 | 19 |  |  |
| *Disodium cromoglycate |  |  |  | 100 | 100 | 100 | 0 |
|  |  |  |  | 30 | 99[2] |  |  |
|  |  |  |  | 10 | 89[3] |  |  |
|  |  |  |  | 3 | 78 |  |  |
|  |  |  |  | 1 | 56[8] |  |  |
|  |  |  |  | 0.3 | 29[5] |  |  |
|  |  |  |  | 0.1 | 19[3] |  |  |

*The superscripts indicate a particular value is an average of two or more determinations.

As regards the dosage regimen of the compounds of this invention, the physician will ultimately determine the dosage which will be most suitable for a particular individual, and it will vary with age, weight and response of the particular patient as well as with the nature and extent of the symptoms, the pharmacodynamic characteristics of the particular agent to be administered, and the route of administration chosen. Generally, small doses will be administered initially, with a gradual increase in the dosage until optimum level is determined. It will often be found that when the composition is administered orally, larger quantities of the active ingredient will be required to produce the same level as produced by a small quantity administered parenterally.

Having full regard for the foregoing factors, it is considered that an effective daily oral dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively alleviate bronchoconstriction in human subjects. These values are illustrative and there may, of course, be individual cases where higher or lower dose ranges are merited.

When administered intravenously or by inhalation, the effective daily dose is from about 0.05 to about 400 mg. per day, and preferably from about 0.25 to 200 mg. per day, or at about 0.005 to 4 mg./kg. of body weight in single or divided doses.

The same two basic changes are present in cases of anaphylactic shock: (1) an increase in permeability of capillaries, and (2) contraction of smooth muscle. The increased capillary permeability is the result of antigenantibody interaction. It, and smooth muscle contraction, can be observed and readily measured. This increase is capillary permeability forms the basis of the PCA test.

The PCA test is a measure of the anti-allergic (especially antiasthmatic) activity of a compound. Compounds which inhibit a positive PCA test induced by the rat immunochemical counterpart of human immunoglobulin E (IgE), or reagin, are considered to have anti-allergic activity (C. Mota, Ann. N.Y. Acad. Sci., 103, 264, 1963). (Reagin is primarily immunoglobulin E (IgE) and is the principal immunoglobulin responsible for allergic asthma, anaphylaxis, hay fever, food sensitivities and certain manifestations of drug sensitivities). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions of a reagin mediated nature.

To put it another way, such compounds block the release of mediators resulting from the antigen-antibody (allergic) reaction as illustrated in the PCA test using rat homocytotropic antibody — a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

EXAMPLE 1

Ethyl 1-Oxo-1H-6-methoxypyrimido[1,2-a]quinoline-2-carboxylate

A. A mixture of 2-amino-4-methoxyquinoline (34 g., 0.196 mole) and diethyl ethoxymethylenemalonate (46.8 g., 0.216 mole) is heated on a steam bath. A clear melt forms within about ten minutes and within about twenty minutes begins to resolidify. The mixture is heated a total of 45 minutes and is then cooled. The product, diethyl 4-methoxy-2-quinolylaminomethylenemalonate, is crystallized from ethanol (350 ml.) as a fluffy solid; m.p. 136.5°–137.5° C.

Analysis: Calc'd for $C_{18}H_{20}N_2O_5$: C, 62.78; H, 5.85; N, 8.14%; Found: C, 62.72; H, 6.10; N, 8.37%

B. To Dowtherm A (350 ml.) at 100° C. is added the product from A (55 g., 0.16 mole) and the resulting clear yellow solution heated to 230°–233° C. for 1.75 hours. The reaction mixture is cooled, diluted with ethyl acetate (500 ml.) and then extracted with 1N hydrochloric acid (3 × 120 ml.). The extracts are combined, made basic with 20% ammonium hydroxide and chilled to precipitate the product. It is filtered and recrystallized successively from ethanol, benzene-cyclohexane (1:1) and ethanol to give 15.5 g. of yellow crystals; m.p. 130°–130.5° C.

Analysis: Calc'd for $C_{16}H_{14}N_2O_4$: C, 64.42; H, 4.73; N, 9.39%; Found: C, 64.38; H, 4.80; N, 9.54 %

EXAMPLE 2

The procedure of Example 1-B is repeated but starting with 3.5 g. of diethyl 4-methoxy-2-quinolylaminomethylenemalonate. The product is recovered by cooling the reaction mixture, diluting it with cyclohexane (150 ml.) to precipitate the crude product as a brown gummy material. It is obtained in crystalline form by heating the diluted reaction mixture to boiling and filtering the hot mixture. Upon cooling the product precipitates as yellow crystals and is separated by filtration. Yield = 1.1 g. Further purification is achieved by recrystallizing it from ethanol.

EXAMPLE 3

Following the procedure of Example 1-A, the compounds listed below are prepared from appropriate reactants. They are recrystallized from suitable solvents such as ethanol, benzene-cyclohexane (1:1) and acetonitrile.

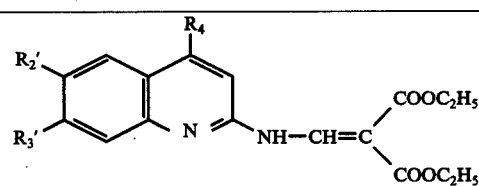

| $R_4$ | $R_2'$ | $R_3'$ | m.p. (° C.) | Calc'd C | H | N | Found C | H | N |
|---|---|---|---|---|---|---|---|---|---|
| OCH₃ | Cl | H | 161–162 | 57.07 | 5.06 | 7.40 | 57.07 | 5.19 | 6.86 |
| OCH₃ | CH₃ | H | 144–146 | 63.67 | 6.19 | 7.82 | 63.67 | 6.15 | 7.63 |
| OCH₃ | OCH₃ | H | 132–133 | 60.96 | 5.92 | 7.48 | 60.80 | 5.87 | 7.32 |
| OCH₃ | H | Cl | 155–157 | 57.07 | 5.06 | 7.40 | 56.89 | 5.08 | 7.29 |
| OCH₃ | H | CH₃ | 139–141 | 63.67 | 6.19 | 7.82 | 63.63 | 6.14 | 7.75 |

-continued

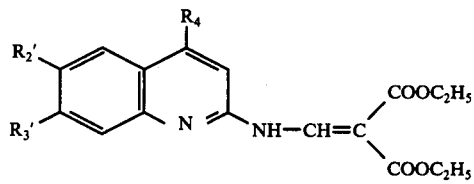

| R₄ | R₂' | R₃' | m.p. (° C.) | Calc'd C | H | N | Found C | H | N |
|---|---|---|---|---|---|---|---|---|---|
| OCH₃ | OCH₃ | OCH₃ | 187–190 | 59.40 | 5.98 | 6.93 | 59.78 | 5.99 | 8.33 |
| OCH₃ | OC₂H₅ | H | 137–138 | 61.84 | 6.62 | 7.21 | 61.60 | 6.19 | 6.98 |
| OC₂H₅ | H | H | 126–127 | 63.67 | 6.18 | 7.81 | 63.63 | 6.21 | 7.79 |
| OCH₃ | H | F | 154–155 | 59.66 | 5.28 | 7.73 | 60.03 | 5.26 | 7.60 |
| OCH₃ | F | H | 140–142 | 59.66 | 5.28 | 7.73 | 59.47 | 5.25 | 7.80 |
| OCH₃ | H | OCH₃ | 145–147 | 60.96 | 5.92 | 7.48 | 60.87 | 5.94 | 7.39 |

EXAMPLE 4

The products of Example 3 are cyclized to the corresponding ethyl 1-oxo-1H-6-methoxypyrimido[1,2-a]quinoline-2-carboxylates by the procedures of Example 2. In most instances, the product separates in the form of crystals upon dilution of the reaction mixture with cyclohexane and hot filtration of the mixture is unnecessary.

The following are thus prepared:

hydrochloric acid (60 ml.) is heated on a steam bath for a half-hour. It is then cooled and filtered to give 0.87 g. of the title product. It is recrystallized from N,N-dimethylformamide; m.p. 219° C. (dec.).

Analysis: Calc'd for $C_{14}H_{10}N_4O_2$: C, 62.22; H, 3.73; N, 10.37% Found: C, 61.60; H, 3.73; N, 10.30%

EXAMPLE 6

The products of Example 4 are hydrolyzed according to the procedure of Example 5 to give:

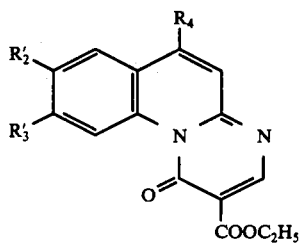

| R₄ | R₂' | R₃' | m.p. (° C.) | Calc'd C | H | N | Found C | H | N |
|---|---|---|---|---|---|---|---|---|---|
| OCH₃ | Cl | H | 213–214 | 57.76 | 3.94 | 8.42 | 57.50 | 3.77 | 8.27 |
| OCH₃ | CH₃ | H | 191.5–192.5 | 65.37 | 5.16 | 8.97 | 65.51 | 5.39 | 8.99 |
| OCH₃ | OCH₃ | H | 200–201.5 | 62.19 | 4.91 | 8.53 | 61.99 | 4.95 | 8.71 |
| OCH₃ | H | OCH₃ | 184–185 | 62.19 | 4.91 | 8.53 | 61.92 | 5.00 | 8.47 |
| OCH₃ | H | Cl | 178–179 | 57.76 | 3.94 | 8.42 | 58.26 | 4.07 | 8.56 |
| OCH₃ | H | CH₃ | 139–141 | 65.37 | 5.16 | 8.95 | 65.11 | 5.25 | 9.02 |
| OCH₃ | OCH₃ | OCH₃ | 215–216 | 60.33 | 5.06 | 7.82 | 60.64 | 5.09 | 7.73 |
| OCH₃ | OC₂H₅ | H | 163.5–164.5 | 63.15 | 5.30 | 8.18 | 63.13 | 5.33 | 8.04 |
| OC₂H₅ | H | H | 143–145 | | | | | | |
| OCH₃ | H | F | 141–143 | 60.76 | 4.14 | 8.85 | 60.44 | 4.51 | 8.37 |
| OCH₃ | F | H | 175.5–177 | 60.76 | 4.14 | 8.85 | 60.86 | 4.18 | 8.80 |

EXAMPLE 5

1-Oxo-1H-6-methoxypyrimido[1,2-a]quinoline-2-carboxylic Acid

A mixture of ethyl 1-oxo-1H-6-methoxypyrimido[1,2-a]quinoline-2-carboxylate (3.0 g.) and concentrated

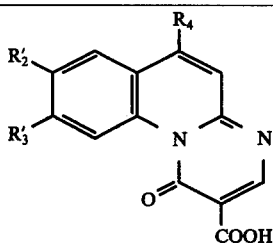

| R$_4$ | R$_2'$ | R$_3'$ | m.p. (° C.) | Calc'd C | Calc'd H | Calc'd N | Found C | Found H | Found N |
|---|---|---|---|---|---|---|---|---|---|
| OCH$_3$ | Cl | H | 239 (dec.) | 55.18 | 2.98 | 9.20 | 54.82 | 3.12 | 9.15 |
| OCH$_3$ | CH$_3$ | H | 247 (dec.) | 63.37 | 4.26 | 9.86 | 63.02 | 4.29 | 9.93 |
| OCH$_3$ | OCH$_3$ | H | | | | | | | |
| OCH$_3$ | H | OCH$_3$ | 230 (dec.) | 60.00 | 4.03 | 9.33 | 59.77 | 4.17 | 9.43 |
| OCH$_3$ | H | Cl | 234 (dec.) | 55.18 | 2.98 | 9.20 | 54.88 | 3.14 | 9.25 |
| OCH$_3$ | H | CH$_3$ | | | | | | | |
| OCH$_3$ | OCH$_3$ | OCH$_3$ | 245 (dec.) | 58.18 | 4.27 | 8.48 | 57.90 | 4.35 | 8.39 |
| OCH$_3$ | OC$_2$H$_5$ | H | 237 (dec.) | 61.14 | 4.49 | 8.92 | 60.73 | 4.56 | 9.04 |
| OC$_2$H$_5$ | H | H | 205 (dec.) | 63.37 | 4.26 | 9.86 | 63.16 | 4.33 | 9.97 |
| OCH$_3$ | H | F | 196–198 (dec.) | | | | | | |
| OCH$_3$ | F | H | 265–268 (dec.) | | | | | | |

EXAMPLE 7

Ethyl 1-Oxo-1H-6-chloropyrimido[1,2-a]quinoline-2-carboxylate

A. A mixture of 2-amino-4-chloroquinoline (15.5 g., 0.087 mole) and diethyl ethoxymethylenemalonate (20.8 g., 0.096 mole) is heated on a steam bath for 45 minutes. Isopropanol (75 ml.) is added to the hot clear melt which is then cooled. The product separates and is filtered, washed with isopropanol and dried. Yield = 26.0 g. of white solid; m.p. 108.5°–109.5° C. It is used directly in step B without further purification.

Recrystallization from ethanol affords an analytical sample, m.p. 109°–110° C.

Analysis: Calc'd for C$_{27}$H$_{17}$N$_2$O$_4$Cl: C, 65.37; H, 5.16; N, 8.97 %; Found: C, 65.18; H, 5.17; N, 9.07 %

B. The intermediate diethyl 4-chloro-2-quinolylaminomethylenemalonate from step A (26 g.) is added to Dowtherm A (75 ml.) at 100° C. The resulting clear solution is heated to 235°–237° C. for 80 minutes and then cooled. Hexane (100 ml.) is added to the reaction mixture and the product which precipitates recovered by filtration, washed with hexane and dried. It is recrystallized from acetonitrile, m.p. 178°–179° C.

Analysis: Calc'd for C$_{15}$H$_{11}$N$_2$O$_3$Cl: C, 59.51; H, 3.66; N, 9.26%; Found: C, 59.02; H, 3.85; N, 9.09 %

The following compounds are similarly prepared from appropriate reactants:

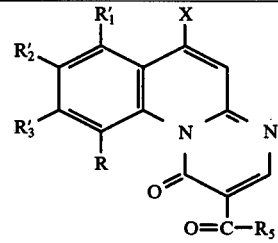

| R$_1'$ | R$_2'$ | R$_3'$ | R | R$_5$ | X |
|---|---|---|---|---|---|
| H | OCH$_3$ | H | H | OC$_2$H$_5$ | Cl |
| H | H | H | OCH$_3$ | OCH$_3$ | Cl |
| H | CH$_3$ | H | CH$_3$ | OCH$_3$ | Cl |
| CH$_3$ | H | H | OCH$_3$ | OC$_2$H$_5$ | Cl |
| H | H | H | Cl | OC$_2$H$_5$ | Cl |
| H | Cl | H | H | O-n-C$_4$H$_9$ | Cl |
| H | H | Cl | H | O-C$_2$H$_5$ | Cl |
| H | H | CH$_3$ | H | OCH$_3$ | Br |
| H | OCH$_3$ | OCH$_3$ | H | OCH$_3$ | Cl |
| H | H | H | H | OC$_2$H$_5$ | Br |
| H | H | H | H | O-n-C$_4$H$_9$ | Br |
| H | CH$_3$ | H | CH$_3$ | OC$_2$H$_5$ | Br |
| H | —CH=CH—CH=CH— | | H | OC$_2$H$_5$ | Cl |

EXAMPLE 8

The following compounds are prepared from the appropriate 2-amino-4-(substituted)quinolines and the appropriate lower alkyl ethoxymethylenemalonates by the procedures of Example 1-A and Example 2.

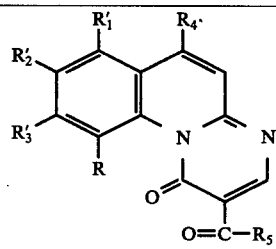

| R$_1'$ | R$_2'$ | R$_3'$ | R | R$_5$ | R$_4$ |
|---|---|---|---|---|---|
| H | H | H | H | OC$_2$H$_5$ | OC$_2$H$_5$ |
| H | H | H | H | OCH$_3$ | O-n-C$_3$H$_7$ |
| H | H | H | H | OCH$_3$ | O-n-C$_4$H$_9$ |
| H | H | H | H | OCH$_3$ | O-i-C$_4$H$_9$ |
| H | Cl | H | H | OC$_2$H$_5$ | O-s-C$_4$H$_9$ |

-continued

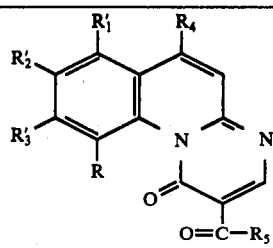

| $R_1'$ | $R_2'$ | $R_3'$ | R | $R_5$ | $R_4$ |
|---|---|---|---|---|---|
| H | Cl | Cl | H | $OC_2H_5$ | $OCH_3$ |
| H | H | Cl | H | $OC_2H_5$ | $O$-n-$C_4H_9$ |
| H | $OCH_3$ | H | H | $OCH_3$ | $O$-n-$C_4H_9$ |
| H | H | $OCH_3$ | H | $O$-n-$C_3H_7$ | $O$-n-$C_4H_9$ |
| $CH_3$ | H | H | $OCH_3$ | $O$-n-$C_4H_9$ | $OCH_3$ |
| H | H | H | $OCH_3$ | $O$-n-$C_4H_9$ | $OCH_3$ |
| H | H | H | Cl | $OCH_3$ | $OCH_3$ |
| H | $CH_3$ | H | $CH_3$ | $OC_2H_5$ | $OCH_3$ |
| H | i-$C_3H_7$ | H | H | $OC_2H_5$ | $OCH_3$ |
| H | —O—$CH_2$—O— | | H | $OC_2H_5$ | $OCH_3$ |
| H | H | | —O—$CH_2$—O— | $OC_2H_5$ | $OCH_3$ |
| H | Br | Cl | H | $OC_2H_5$ | $OCH_3$ |
| $OC_2H_5$ | H | H | $OC_2H_5$ | $OCH_3$ | $O$-n-$C_3H_7$ |
| H | i-$C_3H_7$ | H | i-$C_3H_7$ | $OCH_3$ | $OC_2H_5$ |
| H | —O—$CH_2$—O— | | H | $OCH_3$ | $O$-n-$C_4H_9$ |
| H | H | $SOCH_3$ | H | $OC_2H_5$ | $OC_2H_5$ |
| H | $SOCH_3$ | H | H | $OCH_3$ | $OCH_3$ |
| H | $SCH_3$ | H | H | $OCH_3$ | $OCH_3$ |
| H | H | $SCH_3$ | H | $OC_2H_5$ | $OC_2H_5$ |
| $OCH_3$ | H | H | $OCH_3$ | $OC_2H_5$ | $OCH_3$ |
| H | $O$-n-$C_4H_9$ | $O$-n-$C_4H_9$ | H | $OCH_3$ | $OC_2H_5$ |
| H | $O$-n-$C_3H_7$ | Br | H | $OC_2H_5$ | $OCH_3$ |
| Cl | $O$-n-$C_3H_7$ | H | Cl | $OC_2H_5$ | $OCH_3$ |
| F | H | F | H | $O$-n-$C_3H_7$ | $OCH_3$ |
| F | I | F | H | $OCH_3$ | $OC_2H_5$ |
| Br | $SCH_3$ | Br | H | $OC_2H_5$ | $O$-i-$C_3H_7$ |
| H | H | n-$C_4H_9$ | H | $O$-i-$C_3H_7$ | $OCH_3$ |
| Cl | $O$-n-$C_3H_7$ | Cl | H | $O$-t-$C_4H_9$ | $OCH_3$ |
| H | $SCH_3$ | Cl | H | $OCH_3$ | $O$-n-$C_3H_7$ |
| H | $SOCH_3$ | Cl | H | $OCH_3$ | $O$-n-$C_3H_7$ |
| H | —$OCH_2CH_2O$— | | H | $OC_2H_5$ | $OCH_3$ |
| H | —CH=CH—CH=CH— | | H | $OC_2H_5$ | $OCH_3$ |
| H | —$OCH_2CH_2O$— | | H | $OC_2H_5$ | $OC_2H_5$ |
| H | —$OCH_2CH_2O$— | | H | $OC_2H_5$ | $OCH_2CH=CH_2$ |
| t-$C_4H_9$ | H | H | t-$C_4H_9$ | $OC_2H_5$ | $OCH_3$ |
| H | H | H | $COOCH_3$ | $OC_2H_5$ | $OCH_3$ |
| H | H | $COOCH_3$ | Cl | $OC_2H_5$ | $OCH_3$ |
| H | H | Br | $COOC_2H_5$ | $OCH_3$ | $OCH_3$ |
| Cl | H | $COOCH_3$ | Cl | $OC_2H_5$ | $OCH_3$ |
| $CH_3$ | H | $COOC_4H_9$ | $CH_3$ | $OC_2H_5$ | $OCH_3$ |
| H | $COOCH_3$ | $O$-i-$C_3H_7$ | H | $O$-n-$C_3H_7$ | $OC_2H_5$ |
| H | $COOC_2H_5$ | H | I | $OC_2H_5$ | $OCH_3$ |
| H | H | H | H | $OC_2H_5$ | $OCH_2$—CH=$CH_2$ |
| H | H | $OCH_3$ | H | $OCH_3$ | $OCH$=CH—$C_2H_5$ |
| H | H | H | H | $OC_2H_5$ | $OCH$=C($CH_3$)$CH_3$ |
| H | $OCH_3$ | $OCH_3$ | H | $OC_2H_5$ | $OCH_2CH$=$CHCH_3$ |
| $CH_3$ | H | H | $OCH_3$ | $OC_2H_5$ | $OCH_2$—CH=$CH_2$ |
| H | H | Cl | H | $OCH_3$ | $OCH_2$—CH=$CH_2$ |
| H | H | H | H | $OC_2H_5$ | $OCH_2CH_2C$≡CH |
| H | $OCH_3$ | H | H | $OC_2H_5$ | $OCH_2$—C≡CH |
| H | —O—$CH_2$—O— | | H | $OC_2H_5$ | $OC$≡C—$CH_3$ |
| $OC_2H_5$ | H | H | $OC_2H_5$ | $OC_2H_5$ | $OCH_2$—C≡CH |
| H | H | $COOCH_3$ | Cl | $OC_2H_5$ | $OCH_2$—C≡CH |
| H | $SCH_3$ | Cl | H | $OCH_3$ | $OCH_2$—CH=$CH_2$ |
| H | $SOCH_3$ | Cl | H | $OCH_3$ | $OCH_2$—C≡CH |
| H | $SCH_3$ | $SCH_3$ | H | $OC_2H_5$ | $OCH_3$ |
| H | $SOCH_3$ | $SOCH_3$ | H | $OC_2H_5$ | $OCH_3$ |
| H | —$OCH_2CH_2O$— | | H | $OC_2H_5$ | $OCH_2C$≡CH |
| H | —$OCH_2CH_2O$— | | H | $OC_2H_5$ | $O$-n-$C_5H_{11}$ |
| H | $OCH_3$ | H | H | $OC_2H_5$ | $O$-n-$C_5H_{11}$ |
| H | $OC_2H_5$ | H | H | $OC_2H_5$ | $O$-n-$C_5H_{11}$ |
| H | H | $OCH_3$ | H | $OC_2H_5$ | $O$-i-$C_5H_{11}$ |
| H | $OCH_3$ | $OCH_3$ | H | $OCH_3$ | $O$-i-$C_5H_{11}$ |
| H | —$OCH_2$—O— | | H | $OCH_3$ | $O$-neo-$C_5H_{11}$ |
| $CH_3$ | H | H | $OCH_3$ | $OC_2H_5$ | $O$-i-$C_5H_{11}$ |
| H | H | Cl | H | $O$-n-$C_4H_9$ | $O$-n-$C_5H_{11}$ |
| H | $SOCH_3$ | $SCH_3$ | H | $OCH_3$ | $O$-n-$C_3H_7$ |
| H | Cl | $SCH_3$ | H | $OCH_3$ | $O$-n-$C_3H_7$ |
| H | Cl | $SOCH_3$ | H | $OCH_3$ | $O$-n-$C_3H_7$ |
| H | $SCH_3$ | $SOCH_3$ | H | $OCH_3$ | $O$-n-$C_3H_7$ |

Hydrolysis of the esters according to the procedure of Example 5 affords the corresponding acids.

Ethyl 1-Oxo-1H-6-ethoxypyrimido[1,2-a]quinoline-2-carboxylate

A mixture of p-toluenesulfonic acid monohydrate (20 mg.) and ethyl 1-oxo-1H-6-chloropyrimido[1,2-a]quinoline-2-carboxylate (1.5 g.) in ethanol (75 ml.) is heated at reflux for 24 hours. The solvent is removed under reduced pressure and the residue partitioned between 3N hydrochloric acid (25 ml.)—ethyl acetate (100 ml.). The phases are separated and the ethyl acetate phase extracted with 3N hydrochloric acid (2 × 20 ml.). The acid extracts are combined, made basic with 20% ammonium hydroxide and the resulting precipitate recovered by filtration (235 mg.). It is recrystallized from cyclohexane (20 ml.)—benzene (5 ml.); m.p. 143°–144° C.

Analysis: Calc'd for $C_{17}H_{16}N_2O_4$: C, 65.37; H, 5.16; N, 8.97%; Found: C, 65.18; H, 5.17; N, 9.07%

EXAMPLE 10

The procedure of Example 9 is repeated using the products of Example 7 and the appropriate lower alcohols to give:

| $R_1'$ | $R_2'$ | $R_3'$ | R | $R_5$ | $R_4$ |
|---|---|---|---|---|---|
| H | H | H | H | $OC_2H_5$ | $O$-n-$C_4H_9$ |
| H | H | H | H | $O$-n-$C_4H_9$ | $O$-n-$C_4H_9$ |
| H | $CH_3$ | H | $CH_3$ | $OCH_3$ | $OC_2H_5$ |
| H | $OCH_3$ | H | H | $OC_2H_5$ | $O$-n-$C_3H_7$ |
| H | H | H | $OCH_3$ | $OCH_3$ | $OC_2H_5$ |
| $CH_3$ | H | H | $OCH_3$ | $OC_2H_5$ | $OCH_3$ |
| H | $CH_3$ | H | $CH_3$ | $OC_2H_5$ | $O$-i-$C_3H_7$ |
| H | Cl | H | H | $O$-n-$C_4H_9$ | $OC_2H_5$ |
| H | H | H | Cl | $OC_2H_5$ | $OC_2H_5$ |
| H | H | Cl | H | $OC_2H_5$ | $O$-n-$C_3H_7$ |
| H | H | $CH_3$ | H | $OCH_3$ | $O$-n-$C_3H_7$ |
| H | $OCH_3$ | $OCH_3$ | H | $O$-n-$C_4H_9$ | $OC_2H_5$ |
| H | H | H | H | $OC_2H_5$ | $OCH_2-C\equiv CH_2$ |
| H | H | $OCH_3$ | H | $OC_2H_5$ | $OCH_2-C\equiv CH$ |
| H | H | H | H | $OC_2H_5$ | $O$-n-$C_5H_{11}$ |
| H | $OCH_3$ | H | H | $OC_2H_5$ | $O$-n-$C_5H_{11}$ |

Hydrolysis of the esters according to the procedure of Example 5 affords the corresponding acids.

EXAMPLE 11

2-Hydroxyethyl 1-Oxo-1H-6-methoxypyrimido[1,2-a]-quinoline-2-carboxylates

Triethylamine (1 ml.) is added to a slurry of ethyl 1-oxo-1H-6-methoxypyrimido[1,2-a]quinoline-2-carboxylate (500 mg.) in ethylene glycol (5 ml.). The mixture is stirred for six hours and is then diluted with water (30 ml.). The resulting solution is acidified with acetic acid and the precipitate removed by filtration and recrystallized from N,N-dimethylformamide.

In like manner, the esters of Examples 2–4, 7 and 8 are converted to the 2-hydroxyethyl esters.

Repetition of this procedure but using propylene glycol, 1,4-tetramethylene glycol and 1,5-pentamethylene glycol as reactant affords the corresponding hydroxyalkyl esters.

EXAMPLE 12

Salt Formation

The acid products of Examples 5, 6, 7 and 10 are converted to the sodium, potassium, ammonium, calcium, magnesium, aluminum, triethylamine, tri-n-butylamine, piperidine, triethanolamine, diethylaminoethylamine, pyrrolidine and N,N-dibenzylethylenediamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 13

Injectable Preparation

One thousand grams of ethyl 1-oxo-1H-6-methoxypyrimido[1,2-a]quinoline-2-carboxylate are intimately mixed and ground with 2500 grams of sodium ascorbate. The ground dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

EXAMPLE 14

Tablets

A tablet base is prepared by blending the following ingredients in the proportion by weight indicated:

| Sucrose, U.S.P. | 80.3 |
|---|---|
| Tapioca starch | 13.2 |
| Magnesium stearate | 6.5 |

Into this tablet base there is blended sufficient ethyl 1-oxo-1H-6-methoxypyrimido[1,2-a]quinoline-2-carboxylate to provide tablets containing 20, 100 and 250 mg. of active ingredient per tablet. The compositions are each compressed into tablets, each weighing 360 mg., by conventional means.

EXAMPLE 15

Capsules

A blend is prepared containing the following ingredients:

| Calcium carbonate, U.S.P. | 17.6 |
|---|---|
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient ethyl 1-oxo-1H-6,9-dimethoxypyrimido[1,2-a]quinoline-2-carboxylate to provide capsules containing 10, 25, and 50 mg. of active ingredient per capsule. The compositions are filled into conventional hard gelatin capsules in the amount of 350 mg. per capsule.

In like manner, capsules containing 2.0 mg. and 6.0 mg. of active ingredient, and having 300 mg. of the following blends per capsule are prepared:

| Ingredients | Weight, mg./capsule |
|---|---|
| Drug | 2.00 |
| N-methylglucamine | 18.00 |
| Lactose, Anhydrous | 241.20 |
| Corn starch, Anhydrous | 30.00 |
| *Talc | 8.80 |
| Drug | 6.00 |
| N-methylglucamine | 18.00 |
| Lactose, Anhydrous | 237.20 |
| Corn starch, Anhydrous | 30.00 |
| *Talc | 8.80 |

*Talc added before encapsulation.

EXAMPLE 16

Solution

A solution of ethyl 1-oxo-1H-6,8,9-trimethoxypyrimido[1,2-a]quinoline-2-carboxylate is prepared with the following composition:

| | | |
|---|---|---|
| Effective ingredient | 6.04 | grams |
| Magnesium chloride hexahydrate | 12.36 | grams |
| Monoethanolamine | 8.85 | ml. |
| Propylene glycol | 376.00 | grams |
| Water, distilled | 94.00 | ml. |

The resultant solution has a concentration of effective ingredient of 10 mg./ml. and is suitable for parenteral and, especially, for intramuscular administration.

EXAMPLE 17

An aqueous solution of ethyl 1-oxo-1H-6-methoxypyrimido[1,2-a]quinoline-2-carboxylate (containing 3 mg. of drug per ml. of solution) is placed in a standard nebulizer such as is available from the Vaponephrine Co., Edison, N.J. The solution is sprayed under an air pressure of 6 lbs. per square inch into a closed 8 × 8 × 12 inch plastic container for six minutes. The container has four openings to accomodate the heads of four rats. Four rats are exposed to the drug simultaneously with only their heads coming in contact with aerosol. The results are evaluated as per the PCA reaction test procedure described above.

EXAMPLE 18

Aerosol Suspension

A mixture of ethyl 1-oxo-1H-6-methoxypyrimido[1,2-a]quinoline-2-carboxylate (antiallergy agent) and the other ingredients under (a) in the examples below are micronized to a particle size of 1 to 5 microns in a ball mill. The resulting slurry is then placed in a container equipped with a valve and propellant (b) introduced by pressure filling through the valve nozzle to a guage pressure of approximately 35–40 pounds per square inch at 20° C.

| | Percent |
|---|---|
| Suspension A | |
| (a) Antiallergy agent | 0.25 |
| Isopropyl myristate | 0.10 |
| Ethanol | 26.40 |
| (b) 60–40% mixture of 1,2-dichlorotetrafluoroethane-1-chloropentafluoroethane | 73.25 |
| Suspension B | |
| (a) Antiallergy agent | 0.25 |
| Ethanol | 26.50 |
| (b) 60–40% mixture of 1,2-dichlorotetrafluoroethane-1-chloropentafluoroethane | 73.25 |

PREPARATION A

2-Amino-4-hydroxyquinolines

The appropriate aniline p-toluenesulfonate and ethyl cyanoacetate are combined in equimolar quantities and heated at 225° C. to 260° C. until a melt resulted (Higher temperatures are used if necessary to achieve a melt). The temperature of the melt is lowered to 240°–250° C. and heating continued for one hour. The hot melt is poured into ice-cold chloroform (about 1 to 1.5 liters per mole of aniline reactant) and the mixture stirred for one hour. The solid is filtered off, added to water-ethanol (1 liter of 1:1 per mole of aniline reactant) at 45°–50° C. and the solution made basic with ammonium hydroxide. The solid is separated by filtration and recrystallized from a suitable solvent such as isopropanol.

The following compounds are prepared in this manner.

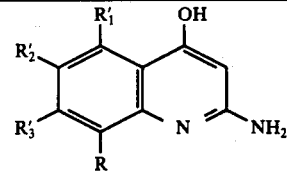

| $R_1'$ | $R_2'$ | $R_3'$ | R |
|---|---|---|---|
| H | i-C3H7 | H | H |
| H | —O—CH2—O— | | H |
| H | H | Cl | H |
| H | SCH3 | H | H |
| H | SOCH3 | H | H |
| H | O-n-C4H9 | O-n-C4H9 | H |
| H | SCH3 | Cl | H |
| H | SOCH3 | Cl | H |
| H | n-C3H7 | Br | H |
| Cl | O-n-C3H7 | H | Cl |
| H | —C=CH—CH=CH— | | H |
| F | H | F | H |
| F | I | F | H |
| Br | SCH3 | Br | H |
| H | H | n-C4H9 | H |
| Cl | Br | Cl | Cl |
| H | i-C3H7 | H | i-C3H7 |
| t-C4H9 | H | H | t-C4H9 |
| H | H | Br | H |
| OC2H5 | H | H | OC2H5 |
| H | H | H | COOCH3 |
| H | H | COOCH3 | Cl |
| H | H | Br | COOC2H5 |
| H | H | COOC4H9 | CH3 |
| H | COOCH3 | O-i-C3H7 | H |
| H | COOC2H5 | H | H |
| H | Cl | SCH3 | H |
| H | Cl | SOCH3 | H |
| H | SCH3 | SOCH3 | H |
| H | SOCH3 | SCH3 | H |

PREPARATION B

Ethers of 2-Amino-4-hydroxyquinoline via Esters of p-Toluenesulfonic Acid

A mixture of the appropriate 2-amino-4-hydroxyquinoline and the appropriate lower alkyl p-toluenesulfonate (10 to 20% molar excess) in xylene (from about 1-2 liters per mole of quinoline compound) is heated at reflux for 4–5 hours. It is then cooled, filtered and the filter cake washed with xylene. The solid is slurried in 3N KOH for 15–20 minutes and then filtered.

The filter cake is washed with water, dried and recrystallized from a suitable solvent.

The 2-amino-4-lower-alkoxyquinoline reactants used in the preceding examples are prepared by this general procedure.

via alkylation with R₄'Br

Equimolar amounts of the appropriate 2-amino-4-hydroxyquinoline and sodium hydride are reacted in warm N,N-dimethylformamide to produce the sodio derivative of the 2-amino-4-hydroxyquinoline. An equimolar amount of the appropriate R₆'Br reactant is added and the reaction mixture heated for 20 minutes on a steam bath. It is then poured into water, the ether product separated by filtration or extracted with a suitable solvent such as benzene or chloroform. The extract is dried (Na₂SO₄) and evaporated. The products are crystallized from suitable solvents.

The alkenyl and alkynyl ethers of the 2-amino-4-hydroxyquinolines used herein are prepared in this manner.

PREPARATION C

2-Amino-4-methoxy-6,7-dimethylthioquinoline

A solution of the sodium salt of methylmercaptan (0.08 mole) in N,N-dimethylformamide (50 ml.) is prepared by bubbling methylmercaptan into a mixture of sodium hydride (3.36 g. of 57% NaH) in N,N-dimethylformamide (100 ml.). The reaction mixture is cooled by means of an ice-bath until the reaction is complete.

The sodium methylmercaptide solution is then added dropwise to a mixture of 2-amino-4-methoxy-6,7-dichloroquinoline (0.04 mole) in N,N-dimethylformamide (50 ml.) cooled in an ice-bath. The mixture is stirred for one hour and then removed from the ice-bath and stirred for an additional two hours. The reaction mixture is poured into water (600 ml.) and the resulting mixture thoroughly stirred. Ether (30 ml.) is added and the precipitate filtered off, washed with ether and dried.

PREPARATION D

2-Amino-4-methoxy-6,7-dimethylsulfinylquinoline

A solution of 2-amino-4-methoxy-6,7-dimethylthylthioquinoline (2 millimoles) in trifluoroacetic acid (4 ml.) is heated to 55° C. on an oil bath. Hydrogen peroxide (452 mg. of 30% H₂O₂, 4 millimoles) is added and the reaction mixture stirred for ten minutes. After cooling to room temperature. absolute ethanol (12 ml.) is added. The resulting precipitate is filtered off, washed with ether and dried. It is recrystallized from ethanol.

PREPARATION E

Ethyl 1-Oxo-1H-6-hydroxypyrimido[1,2-a]quinoline-2-carboxylate

A mixture of ethyl 1-oxo-1H-6-methoxypyrimido[1,2-a]quinoline-2-carboxylate (596 mg., 2.0 millimoles) in 30% HBr in acetic acid (20 ml.) is heated at reflux for 3.5 hours. The reaction mixture is then cooled and the product, 1-oxo-1H-6-hydroxypyrimido[1,2-a]quinoline-2-carboxylic acid, filtered off. It is recrystallized from N,N-dimethylformamide. Yield = 160 mg.; m.p. 268.5° C. (dec.).

Analysis: Calc'd for $C_{13}H_8O_4N_2$: C, 60.94; H, 3.14; N, 10.94% Found: C, 60.40; H, 3.20; N, 10.92%

The acid is esterified by refluxing with excess ethanol in the presence of 3% hydrochloric acid as catalyst for four hours. The excess ethanol is then removed by distillation, the residue diluted with water and then treated with solid sodium carbonate until any acid present is removed. The title product is filtered off, washed with water and dried.

What is claimed is:

1. A compound of the formula

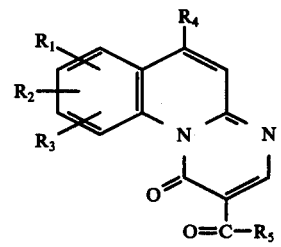

wherein each of the benzenoid substituents $R_1$, $R_2$ and $R_3$ is selected from the group consisting of hydrogen, alkoxy having from 1 to 5 carbon atoms, carboalkoxy having from 1 to 5 carbon atoms in the alkoxy group, fluoro, chloro, bromo, methylthio, methylsulfinyl and alkyl having from 1 to 5 carbon atoms; with the proviso that no more than two of $R_1$, $R_2$ and $R_3$ are bulky branched chain alkyl or branched chain alkoxy groups and when two of said $R_1$, $R_2$ and $R_3$ are bulky groups they are located on non-adjacent positions;

$R_2$ and $R_3$ when taken together are selected from the group consisting of 1,3-butadienyl and alkylenedioxy of 1 to 2 carbon atoms;

$R_4$ is selected from the group consisting of chloro, bromo and $OR_4'$ wherein $OR_4'$ is selected from the group consisting of alkoxy having from 1 to 5 carbon atoms, alkenyloxy of 3 to 4 carbon atoms and alkynyloxy of 3 to 4 carbon atoms;

$R_5$ is selected from the group consisting of hydroxy, alkoxy having from 1 to 5 carbon atoms and hydroxy substituted alkoxy having from 2 to 5 carbon atoms;

and the pharmaceutically-acceptable cationic salts of those compounds wherein $R_5$ is hydroxy.

2. A compound according to claim 1 wherein each of $R_1$, $R_2$ and $R_3$ is selected from the group consisting of hydrogen, alkoxy, fluoro and alkyl;

$R_5$ is selected from the group consisting of hydroxy and alkoxy;

$R_4$ is $OR_4'$ wherein $OR_4'$ is alkoxy;

and the pharmaceutically-acceptable cationic salts of those compounds wherein $R_5$ is hydroxy.

3. A compound according to claim 1 wherein each of $R_1$, $R_2$ and $R_3$ is selected from the group consisting of hydrogen, alkoxy, fluoro and alkyl;

$R_5$ is selected from the group consisting of hydroxy and alkoxy;

$R_4$ is selected from the group consisting of chloro and bromo; and the pharmaceutically-acceptable cationic salts of those compounds wherein $R_5$ is hydroxy.

4. A compound according to claim 2 wherein each of $R_1$, $R_2$ and $R_3$ is hydrogen; $R_5$ is alkoxy; and $R_4$ is methoxy.

5. A compound according to claim 2 wherein each of $R_1$, $R_2$ and $R_3$ is hydrogen; $R_5$ is hydroxy; and $R_4$ is alkoxy.

6. A compound according to claim 2 wherein at least one and not more than two of the benzenoid substituents $R_1$, $R_2$ and $R_3$ is alkoxy, the remaining benzenoid substituents being hydrogen; $R_5$ is alkoxy and $R_4$ is methoxy.

7. A compound according to claim 2 wherein $R_1$ is hydrogen, $R_2$ is 8-alkoxy, $R_3$ is 9-alkoxy, $R_5$ is alkoxy and $R_4$ is methoxy.

8. A compound according to claim 1 wherein $R_2$ and $R_3$ when taken together are alkylenedioxy; $R_1$ is hydrogen; $R_5$ is alkoxy and $R_4$ is methoxy.

9. The compound according to claim 4 wherein $R_5$ is ethoxy.

10. The compound according to claim 5 wherein $R_4$ is methoxy.

11. The compound according to claim 5 wherein $R_4$ is ethoxy.

12. The compound according to claim 6 wherein $R_2$ is 8-methoxy; each of $R_1$ and $R_3$ is hydrogen; and $R_5$ is ethoxy.

13. The compound according to claim 8 wherein $R_2$ and $R_3$ when taken together are 8,9-methylenedioxy; and $R_5$ is ethoxy.

14. The method of treating bronchial asthma in a mammalian subject requiring such treatment which comprises administering to said subject an anti-bronchial effective amount of a compound having the formula

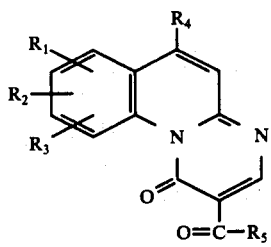

wherein each of the benzenoid substituents $R_1$, $R_2$ and $R_3$ is selected from the group consisting of hydrogen, alkoxy having from 1 to 5 carbon atoms, carboalkoxy having from 1 to 5 carbon atoms in the alkoxy group, fluoro, chloro, bromo, methylthio, methylsulfinyl and alkyl having from 1 to 5 carbon atoms; with the proviso that no more than two of $R_1$, $R_2$ and $R_3$ are bulky branched chain alkyl or branched chain alkoxy groups and when two of said $R_1$, $R_2$ and $R_3$ are bulky groups they are located on non-adjacent positions;

$R_2$ and $R_3$ when taken together are selected from the group consisting of 1,3-butadienyl and alkylenedioxy of 1 to 2 carbon atoms;

$R_4$ is selected from the group consisting of chloro, bromo and $OR_4'$ wherein $OR_4'$ is selected from the group consisting of alkoxy having from 1 to 5 carbon atoms, alkenyloxy of 3 to 4 carbon atoms and alkynyloxy of 3 to 4 carbon atoms;

$R_5$ is selected from the group consisting of hydroxy, alkoxy having from 1 to 5 carbon atoms and hydroxy substituted alkoxy having from 2 to 5 carbon atoms;

and the pharmaceutically-acceptable cationic salts of those compounds wherein $R_5$ is hydroxy.

15. The method according to claim 14 wherein each of $R_1$, $R_2$ and $R_3$ is hydrogen; $R_5$ is alkoxy; and $R_4$ is methoxy.

16. The method according to claim 14 wherein each of $R_1$, $R_2$ and $R_3$ is hydrogen; $R_5$ is hydroxy; and $R_4$ is alkoxy.

17. The method according to claim 14 wherein at least one and not more than two of the benzenoid substituents $R_1$, $R_2$ and $R_3$ is alkoxy, the remaining benzenoid substituents being hydrogen; $R_5$ is hydroxy; and $R_4$ is methoxy.

18. The method according to claim 15 wherein $R_5$ is ethoxy.

19. The method according to claim 16 wherein $R_4$ is methoxy.

20. The method according to claim 17 wherein $R_3$ is 9-methoxy; and each of $R_1$ and $R_2$ is hydrogen.

21. A pharmaceutical composition useful in treating bronchial asthma in a mammalian subject requiring such treatment which comprises a pharmaceutically-acceptable carrier and a compound of the formula

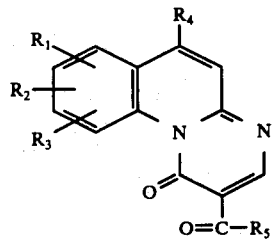

wherein each of the benzenoid substituents $R_1$, $R_2$ and $R_3$ is selected from the group consisting of hydrogen, alkoxy having from 1 to 5 carbon atoms, carboalkoxy having from 1 to 5 carbon atoms in the alkoxy group, fluoro, chloro, bromo, methylthio, methylsulfinyl and alkyl having from 1 to 5 carbon atoms; with the proviso that no more than two of $R_1$, $R_2$ and $R_3$ are bulky branched chain alkyl or branched chain alkoxy groups, and when two of said $R_1$, $R_2$ and $R_3$ are bulky groups they are located on nonadjacent positions;

$R_2$ and $R_3$ when taken together are selected from the group consisting of 1,3-butanediol and alkylenedioxy of 1 to 2 carbon atoms;

$R_5$ is selected from the group consisting of hydroxy, alkoxy having from 1 to 5 carbon atoms; and hydroxy substituted alkoxy having from 2 to 5 carbon atoms;

$R_4$ is selected from the group consisting of chloro, bromo and $OR_4'$ wherein $OR_4'$ is selected from the group consisting of alkoxy having from 1 to 5 carbon atoms, alkenyloxy of 3 to 4 carbon atoms and alkynyloxy of 3 to 4 carbon atoms;

and the pharmaceutically-acceptable cationic salts of those compounds wherein $R_5$ is hydroxy.

22. A composition according to claim 21 wherein each of $R_1$, $R_2$ and $R_3$ is hydrogen; $R_5$ is alkoxy and $R_4$ is methoxy.

23. A composition according to claim 21 wherein each of $R_1$, $R_2$ and $R_3$ is hydrogen; $R_5$ is hydroxy and $R_4$ is alkoxy.

24. A composition according to claim 21 wherein $R_5$ is alkoxy; $R_4$ is methoxy; and at least one and not more than two of the benzenoid substituents $R_1$, $R_2$ and $R_3$ is alkoxy, the remaining benzenoid substituents being hydrogen.

25. A pharmaceutical composition as claimed in claim 21 in a form suitable for administration by inhalation.

* * * * *